(12) United States Patent
Bhagat et al.

(10) Patent No.: US 10,350,309 B2
(45) Date of Patent: Jul. 16, 2019

(54) METHODS OF PREPARING OPHTHALMIC FORMULATIONS AND USES OF SAME

(71) Applicant: Cognoptix, Inc., Acton, MA (US)

(72) Inventors: Haresh Bhagat, Fort Worth, TX (US); Gerald D. Cagle, Fort Worth, TX (US); Francis X. Smith, Salem, NH (US); Paul D. Hartung, Acton, MA (US)

(73) Assignee: Cognoptix, Inc., Concord, MA (US)

( * ) Notice: Subject to any disclaimer, the term of this patent is extended or adjusted under 35 U.S.C. 154(b) by 0 days.

(21) Appl. No.: 15/864,679

(22) Filed: Jan. 8, 2018

(65) Prior Publication Data

US 2018/0126008 A1 May 10, 2018

Related U.S. Application Data

(63) Continuation of application No. 14/528,077, filed on Oct. 30, 2014.

(60) Provisional application No. 61/898,131, filed on Oct. 31, 2013.

(51) Int. Cl.
*A61K 49/00* (2006.01)
*A61K 9/00* (2006.01)
*A61K 47/06* (2006.01)

(52) U.S. Cl.
CPC ........ *A61K 49/0021* (2013.01); *A61K 9/0048* (2013.01); *A61K 47/06* (2013.01)

(58) Field of Classification Search
CPC ... A61K 49/0021; A61K 9/0048; A61K 47/06
See application file for complete search history.

(56) References Cited

U.S. PATENT DOCUMENTS

| 3,764,616 A | 10/1973 | Elks et al. | |
| 8,940,918 B2 | 1/2015 | Yang et al. | |
| 2003/0144635 A1* | 7/2003 | Connor | A61K 9/0014 604/294 |
| 2015/0118163 A1 | 4/2015 | Bhagat et al. | |

FOREIGN PATENT DOCUMENTS

| EP | 2 420 179 A2 | 2/2012 | |
| EP | 2420179 A2 * | 2/2012 | ........... A61B 3/0008 |
| JP | S48-38701 B1 | 11/1973 | |
| JP | 5-253508 | 10/1993 | |
| JP | 2013-513619 A | 4/2013 | |
| JP | 2013-534171 A | 9/2013 | |
| WO | 2008/144065 A1 | 11/2008 | |
| WO | WO-2008144065 A1 * | 11/2008 | ........... A61K 9/0048 |
| WO | 2011/072257 A2 | 6/2011 | |
| WO | WO-2011072257 A2 * | 6/2011 | ........... C07C 255/42 |
| WO | 2012/024188 A1 | 2/2012 | |
| WO | 2015066270 A1 | 5/2015 | |

OTHER PUBLICATIONS

Remington: The Science and Practice of Pharmacy, 1985, pp. 1576, 1599.*
Webpage printout, ("www.quackco.com/YTZ.html," accessed Aug. 30, 2017).*
Seizai kikai gijutsu handbook, 2nd edition, Chijinshokan Co., Ltd., pp. 682 to 685, 2010.
Tosoh, "Enviornmentally friendly products with superior grinding efficiency." https://www.tosoh.com/our-products/advanced-materials/zirconia-grinding--dispersion-media, retrieved on Sep. 28, 2018.
English Translation of Japanese Office Action for Japanese Patent Application No. 2016-527235 dated Jun. 27, 2018 entitled "Methods of Preparing Ophthalmic Formulations and Uses of Same".
"IKA ULTRS TURRAX Ball Mill Tube 50m:, Stainless Steel", Downloaded Aug. 26, 2013, 2 pages. URL: http://www.coleparmer.com/Product/IKA_ULTRA_TURRAX_Ball_Mill_Tube_50_mL_s . . . .
Sigma-Aldrich, "Fluorescent Molecular Rotors", downloaded May 31, 2013, 1 page. URL: http://www.sigmaaldrich.com/life-science/biochemicals/biochemical-products.
Apte, S.P., et al., "Use of Sodium Chloride to FAcilitate Reductions of Partide Size of Dexamethasone During Ball Milling", Drug Development and Industrial Pharmacy, 29(3):367-373 (2003).
Dunsford, H.A., et al., "Investigation on Nonhuman Systems", Journal of the National Cancer Institute, 73:161-168 (1984).
Gèze, A., et al., "Development of 5-iodo-2'-deoxyuridine Milling Process to Reduce Initial Burst Release from PLGA Microparticles", International Journal of Pharmaceutics, 178:257-268 (1999).
Harper, M.J.K. and Walpole, A.L., "A New Derivative of Triphenylethylene: Effect on Implantation and Mode of Action in Rats", J. Reprod. Fert., 13:101-119 (1967).
Henry, M.C., et al., "Respiratory Tract Tumors in Hamsters Induced by Benzo(a)pyrene", Cancer Research, 33:1585-1592 (1973).

(Continued)

*Primary Examiner* — Robert S Cabral
(74) *Attorney, Agent, or Firm* — Hamilton, Brook, Smith & Reynolds, P.C.

(57) ABSTRACT

The present invention relates to a process for preparing an ointment comprising subjecting a mixture of a fluorescent molecular rotor compound, mineral oil, and grinding media to ball milling agitation and combining this mixture with a hydrophobic vehicle for an ointment. The invention also relates to an ophthalmic formulation comprising a pharmaceutically acceptable carrier and a compound of the following structural Formula (I), or a pharmaceutically acceptable salt thereof:

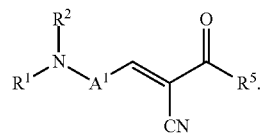

Values and preferred values of the variables in structural Formula (I) are described herein.

10 Claims, No Drawings

(56) References Cited

OTHER PUBLICATIONS

Patterson, J.E., et al., "Preparation of Glass Solutions of Three Poorly Water Soluble Drugs by Spray Drying, Melt Extrusion and Ball Milling", International Journal of Pharmaceutics, 336:22-34 (2007).

Notification of Transmittal of the International Search Report (ISR) and the Written Opinion (WO) of the International Searching Authority, or the Declaration with copies of the ISR and WO, PCT/US2014/063059, entitled "Methods of Preparing Ophthalmic Formulations and Uses of Same", dated Jan. 19, 2015.

International Preliminary Report on Patentability and the Written Opinion of the International Searching Authority for International Application No. PCT/US2014/063059, entitled "Methods of Preparing Ophthalmic Formulations and Uses of Same", dated May 3, 2016.

Australian Examination Report for International Application No. AU 2014342327, entitled "Methods of Preparing Ophthalmic Formulations and Uses of Same," dated Oct. 10, 2016.

Non-Final Office Action for U.S. Appl. No. 14/528,077, dated Jan. 9, 2017.

Final Office Action for U.S. Appl. No. 14/528,077, dated Sep. 7, 2017.

Examination Report for New Zealand Application No. 719983, entitled, "Methods of Preparing Opthalmic Formulations and Uses of Same," dated Jul. 13, 2017.

\* cited by examiner

METHODS OF PREPARING OPHTHALMIC FORMULATIONS AND USES OF SAME

RELATED APPLICATION

This application is a continuation of U.S. application Ser. No. 14/528,077, filed Oct. 30, 2014, which claims the benefit of U.S. Provisional Application No. 61/898,131, filed on Oct. 31, 2013. The entire teachings of the above applications are incorporated herein by reference.

BACKGROUND OF THE INVENTION

Early diagnosis and detection of diseases and disease risk generally improves disease prognosis and expands treatment options. Recently, it has been discovered that analyzing the lenses of the eyes can yield indications of various types of diseases. For example, neurodegenerative disease such as an amyloidogenic disorders have recently been linked to the presence or increase in the amount of aggregate in the supranuclear region and/or cortical lens region of the eye. An example of an amyloidogenic disorder is Alzheimer's disease (AD), which is characterized by a progressive loss of cognitive abilities including memory loss, personality changes, and impaired reasoning. Innovative formulations and processes for preparing formulations such as ophthalmic formulations and diagnostic ointments for diagnosis and detection of neurodegenerative diseases will help alleviate the burden of these health issues.

SUMMARY OF THE INVENTION

It has now been discovered that an ointment comprising a fluorescent molecular rotor compound possesses advantageous properties (e.g., uniformity of particle content) when it is manufactured by methods described and claimed herein. For example, it has been found that by using the method described and claimed herein an ointment is obtained that is suitable for use in the eye of a subject, in particular for diagnostic purposes. It has been found that the method is particularly advantageous in the case of fluorescent molecular rotor compounds. By applying the method, a fluorescent molecular rotor compound, which is provided in particulate form, is transformed to a mixture of particles with uniform particle size distribution without significant loss of compound material. In example embodiments, a process for preparing an ophthalmic formulation comprising a fluorescent molecular rotor compound provides a formulation useful to diagnose and to assess disease risk for amyloidogenic disorders. In some embodiments, the ophthalmic formulation used to diagnose and assess disease risk for amyloidogenic disorders is an ointment. For example, ointments of the present invention can be manufactured by a method comprising:

(a) combining a fluorescent molecular rotor compound with mineral oil as a levigating agent, thereby obtaining a first mixture;
(b) subjecting the first mixture to ball milling agitation with a grinding media, thereby obtaining a second mixture; and
(c) combining the second mixture with a hydrophobic vehicle, thereby obtaining an ointment.

In one embodiment, the fluorescent molecular rotor compound is represented by structural Formula (I), or a pharmaceutically acceptable salt thereof:

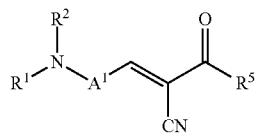

wherein:

$A^1$ is an optionally substituted C6-C18 arylene, an optionally substituted C5-C18 heteroarylene, or is represented by the following structural formula:

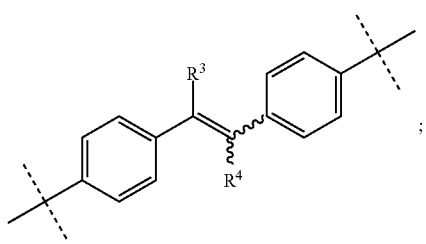

$R^1$ and $R^2$ are each independently hydrogen, optionally substituted C1-C12 alkyl, an optionally substituted C1-C12 heteroalkyl, optionally substituted C3-C12 cycloalkyl, or $R^1$ and $R^2$ taken together with the nitrogen atom to which they are attached form an optionally substituted 3 to 12 membered heterocycloalkyl;

$R^3$ and $R^4$ are each independently hydrogen, methyl, or ethyl;

$R^5$ is —OH, optionally substituted —O(C1-C6 alkyl), —NR$^6$R$^7$ or is represented by the following structural formula:

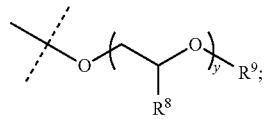

$R^6$ and $R^7$ are each independently, hydrogen, methyl, ethyl or $R^6$ and $R^7$ taken together with the nitrogen atom to which they are attached form a 5 to 7 membered heterocycloalkyl containing one to three ring heteroatoms independently selected from N, O, and S;

wherein:

y is an integer from 1 to 10;

$R^8$, for each occurrence independently, is hydrogen, —OH, or —CH$_2$OH;

$R^9$ is hydrogen, —NR$^{10}$R$^{11}$, —C(O)R$^{12}$, optionally substituted C1-C6 alkyl, optionally substituted C1-C6 heteroalkyl;

$R^{10}$, $R^{11}$ and $R^{12}$ are each independently hydrogen or C1-C6 alkyl.

In some embodiments, the present invention relates to a process for preparing an ointment, preferably an ophthalmic ointment, comprising:

a) combining a fluorescent molecular rotor compound of the following structural formula:

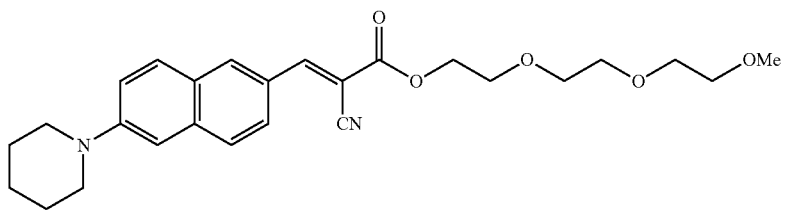 [SMILES: COCCOCCOCCOC(=O)/C(C#N)=C/c1ccc2cc(N3CCCCC3)ccc2c1]

with mineral oil as a levigating agent, thereby obtaining a first mixture;

b) subjecting the first mixture to ball milling agitation, thereby obtaining a second mixture; and c) combining the second mixture with a hydrophobic vehicle, thereby obtaining an ointment.

In some embodiments, the present invention relates to an ophthalmic formulation comprising a fluorescent molecular rotor compound represented by structural Formula (I), structural Formula (II), structural Formula (III), or a pharmaceutically acceptable salt thereof and a pharmaceutically acceptable carrier.

In certain embodiments, a process for preparing an ophthalmic ointment comprising a fluorescent molecular rotor compound and mineral oil subjected to ball milling agitation provides a formulation with enhanced uniformity of content compared to formulations prepared by other processes. Enhanced uniformity of content can include uniformity of particle size and uniformity of dispersion of the fluorescent molecular rotor compound particles. For example, particles of the fluorescent molecular rotor compound having a size distribution characterized by a d(0.95) particle size of less than about 10 microns. For example, particle dispersion and particle size uniformity can be enhanced when the process comprises grinding media or grinding beads with an average particle size of at least 3 mm for ball milling agitation.

Ophthalmic formulations and ointments prepared by processes of the invention involving ball milling agitation can provide more stable and uniform formulations, thus facilitating administration of the formulation to the eye and allowing for more precise dosing of the active compound. In addition, the uniform particle size distribution renders it feasible to provide formulations that are potentially less irritating to, e.g., the eye than formulations prepared using other processes. In some embodiments, the formulations are useful in eye tests for diagnosing amyloidogenic disorders. In a preferred embodiment, the formulations are useful for aiding in the diagnosis of, and to assess disease risk, for amyloidogenic disorders in an eye test.

DETAILED DESCRIPTION OF THE INVENTION

A description of example embodiments of the invention follows.

Glossary

"Alkyl" used alone or as part of a larger moiety such as "haloalkyl" or "alkoxyalkyl" refers to a straight or branched, saturated aliphatic group having the specified number of carbons, typically having 1 to 12 carbon atoms. More particularly, the aliphatic group may have 1 to 8, 1 to 6, or 1 to 4 carbon atoms. Alkyl is exemplified by groups such as methyl, ethyl, n-propyl, isopropyl, n-butyl, isobutyl, tert-butyl, n-hexyl, and the like.

"Heteroalkyl" refers to a 1 to 12 membered straight or branched, saturated aliphatic group having one to three heteroatoms independently selected from nitrogen, oxygen and sulfur. Examples of heteroalkyl groups include ethylenediamine, hexylamine, and the like.

"Cycloalkyl" refers to a 3 to 12 membered fully saturated or partially unsaturated monocyclic ring system. Examples of cycloalkyl groups include cyclohexane, cyclopentane, cycloundecane, and the like.

"Heterocycloalkyl" refers to a 3 to 7 membered fully saturated or partially unsaturated monocyclic ring system, containing one to three ring heteroatoms independently selected from nitrogen, oxygen and sulfur. Examples of optionally substituted heterocycloalkyl groups include piperidine, ($C_1$-$C_4$)alkylpiperidine, morpholine, piperazine, succinimide, and the like.

"Halogen" and "halo" refer to fluoro, chloro, bromo or iodo.

"Cyano" refers to the group —CN.

"Carbonyl" refers to a divalent —C(O)— group.

"Aryl" refers to an aromatic carbocyclic group of from 6 to 18 carbon atoms having a single ring or multiple condensed rings. The term "aryl" also includes aromatic carbocycle(s) fused to cycloalkyl or heterocycloalkyl groups. Examples of aryl groups include phenyl, benzo[d][1,3]dioxole, naphthyl, phenantrenyl, and the like.

"Arylene" refers to a disubstituted aryl group as defined above.

"Heteroaryl" refers to a 5 to 18 membered monocyclic, bicyclic or tricyclic heteroaromatic ring system, containing one to four ring heteroatoms independently selected from nitrogen, oxygen and sulfur. The term "heteroaryl" also includes heteroaromatic ring(s) fused to cycloalkyl or heterocycloalkyl groups. Particular examples of heteroaryl groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, phthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 1,2,3,4-tetrahydroquinolyl, 1,2,3,4-tetrahydroisoquinolyl, purinyl, pteridinyl, carbazolyl, xanthenyl, benzoquinolyl, and the like.

"Heteroarylene" refers to a disubstituted heteroaryl group as defined above.

"Stilbene" refers to a diarylethene and is represented by the following structural formula:

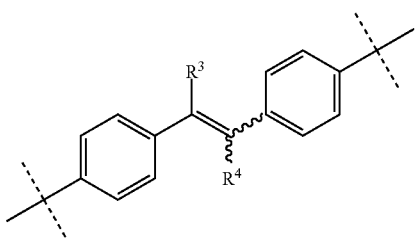

In the above structural formula, the use of a wavy line "〜" indicates that the substituents $R^3$ and $R^4$ can be either in the E or in the Z configuration.

"Amino" means —$NH_2$. "Alkylamine" and "dialkylamine" mean —NHR and —$NR_2$, respectively, wherein R is an alkyl group.

Suitable substituents for "alkyl", "cycloalkyl", "arylene", etc., are those which will form a stable compound of the invention. Examples of suitable substituents are those selected from the group consisting of hydrogen, halogen, —CN, —OH, —$NH_2$, ($C_1$-$C_4$)alkyl, ($C_1$-$C_4$)haloalkyl, ($C_3$-$C_7$)cycloalkyl, (5-7 membered)heterocycloalkyl, ($C_1$-$C_4$)alkyl(5-7 membered)heterocycloalkyl, (5-7 membered)heterocycloalkyl($C_1$-$C_4$)alkyl, —NH($C_1$-$C_6$)alkyl, —N(($C_1$-$C_6$)alkyl)$_2$, ($C_1$-$C_6$)alkoxyalkyl, ($C_1$-$C_6$)alkoxycarbonyl, —$CONH_2$, —$OCONH_2$, —CONH($C_1$-$C_4$)alkyl, —OCONH($C_1$-$C_4$)alkyl, —CON(($C_1$-$C_4$)alkyl)$_2$, —CO($C_1$-$C_4$)alkyl, —OCO($C_1$-$C_4$)alkyl, —C(O)O($C_1$-$C_4$)alkyl, —OC(O)O($C_1$-$C_4$)alkyl, —C(O)H or —$CO_2H$. For example, suitable substituents can be selected from the group consisting of hydrogen, methyl, —OMe, —N(($C_1$-$C_6$)alkyl)$_2$, piperidine, morpholine, piperazine, 1-methylpiperazine, and 2-morpholinoethanamine.

Pharmaceutically acceptable salts of the compounds disclosed herein are included in the present invention. For example, an acid salt of a compound containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, triethiodide, and trifluoroacetate salts.

Salts of the compounds containing an acidic functional group can be prepared by reacting with a suitable base. Such a pharmaceutically acceptable salt can be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

A "fluorescent molecular rotor compound" is a compound with the ability to form an excited state through the rotation of one portion of the compound structure with respect to the rest of the molecule. The emission of the fluorescent molecular rotor compound depends, for example, on the polarity and the viscosity of the microenvironment surrounding the compound. The fluorescent molecular rotor compound fluoresces after photon absorption when the rotation is constrained, for example, by dye aggregation, protein binding, and solvent interactions. Emission is blocked in microenvironments where fluorescent molecular rotor compound rotates freely.

The fluorescent molecular rotor compounds of the invention may possess one or more chiral centers or double bonds and so exist in a number of stereoisomeric forms. All stereoisomers, racemates, diastereomers, tautomers, geometric isomers, individual isomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

Fluorescent molecular rotor compounds suitable for use in the present invention include, but are not limited to the fluorescent molecular rotor compound categories and specific fluorescent molecular rotor compounds listed below and the fluorescent molecular rotor compounds represented by Formula (I), Formula (II), and Formula (III).

As used herein, the phrases "ball milling" or "ball milling agitation" refer to a process of grinding that uses a container partially filled with material to be ground combined with a grinding media that rotates around an axis to reduce particle size and, if needed, to disperse the particles in a suitable vehicle. The ball milling process of the invention preferably results in approximately spherical or ellipsoidal particles.

As used herein, a "mill speed" refers to the speed of rotating a container as described in the above paragraph in a ball milling process. The mill speed at which all grinding media (or grinding beads) are forced to the internal surface of a ball milling container is a "critical mill speed," and no desired grinding occurs at or above critical mill speed. In some embodiments, the ball milling agitation occurs at a mill speed expressed as some percentage of critical mill speed, for example at greater than 30% of critical mill speed. In another embodiment, the ball milling agitation occurs at about 50% to about 70% of critical mill speed.

As used herein, a "grinding media" or "grinding beads" refers to material, preferably an inert material, used in a balling milling process. Several parameters determine the performance of a given material in a ball milling process. Typically, a material is selected with a crushing strength and a wear resistance, which is preferably greater than that of the container used in the milling process. In addition, a suitable grinding material has a higher density than the material which is to subjected to the grinding process. For example, the grinding media consists of materials including ceramics, glass, steel, and agate. For example, the ceramic grinding material is selected from magnesia stabilized zirconia, zirconium silicate, zirconia stabilized alumina, alumina-zirconia composite, burundum, and yttrium stabilized zirconia. In some embodiments, the grinding media can have a spherical, a bead, a rod, or a natural shape. In a preferred embodiment, the grinding media comprises ceramic beads, preferably yttrium stabilized zirconia beads. In a preferred embodiment, the grinding media comprises beads with an average diameter in the range from 0.1 to 25 mm, preferably in the range from 0.5 to 15 mm, more preferably in the range from 2 mm to 10 mm, even more preferably in the range from 3 to 8 mm, most preferably in the range from 4 to 6 mm. In another embodiment, the grinding media comprises beads having a diameter of 5 mm. Preferably, the grinding media comprises ceramic beads having a diameter of 5 mm. In some embodiments, larger bead sizes are preferable over smaller bead sizes. In particular, it may be preferred in such embodiments to use bead sizes of more than 2 mm in diameter, preferably from 4 to 10 mm in diameter. Such larger bead sizes may in some embodiments allow to obtain smaller particle sizes, which may again be preferable to ensure homogenous particle size distribution.

As used herein, "size distribution" of particles refers to the number of particles in a first mixture or in a second mixture as defined above that fall into each of various size ranges given as a percentage of the total number of all sizes in the sample of interest. An important characteristic of the size distribution of particles is the d(0.95), which is the size, in microns, below which 95% by volume of the particles are found. Thus, a d(0.95) of less than 10 microns (μm) means that 95 percent by volume of the particles in a composition have a diameter less than 10 microns. In a preferred embodiment of the invention, at least 90%, the d(0.9), preferably at least 95%, the d(0.95), even more preferably at least 99%, the d(0.99) of the particles in a second mixture or in an ophthalmic ointment, respectively, have a diameter of less than 10 μm, wherein less than 10%, preferably less than 5%, more preferably less than 2% of the particles have a diameter of less than 5 μm.

As used herein, "median particle diameter" refers to a particle diameter, with respect to which 50% of the particles have a smaller diameter and 50% of the particles have a larger diameter in the sample of interest. For example, a d(0.5) of less than 10 μm means that 50% by volume of the particles in a composition have a diameter less than 10 μm, which corresponds to a median particle diameter of less than 10 μm. The median particle diameter represents the particle diameter in the middle of all sizes of particles in the sample of interest. In one embodiment, the median particle diameter is less than 10 μm, preferably less than 9 μm, more preferably less than 8 μm, even more preferably less than 7 μm and most preferably less than 6 μm. Preferably, the median particle diameter is in the range from 2 to 10 μm, more preferably in the range from 3 to 8 μm and even more preferably from 4 to 7 μm. Most preferably, the median particle diameter is between 4 and 6 μm. For such preferable median particle sizes, the size distribution of particles also has certain values, preferably the d(0.90), more preferably the d(0.95) value of less than 10 μm.

As used herein, a "hydrophobic vehicle" includes any vehicle or mixture of vehicles that are insoluble or have very limited solubility in water. The hydrophobic vehicle, for example, is suitable for administration to the eye. In particular, the hydrophobic vehicle is tolerated by the ocular tissue. A hydrophobic vehicle is also a non-aqueous medium. For example, the hydrophobic vehicle is selected from one or more of a petrolatum, a mineral oil, a polyglycol, a silicone oil, a fluorocarbon, a lanolin, a gelled mineral oil, and a surfactant.

A "petrolatum" is a semi-solid mixture of saturated hydrocarbons obtained from petroleum. For example, a petrolatum includes petroleum jelly, white petrolatum, white petroleum, yellow petrolatum, red petrolatum, soft paraffin, paraffin jelly, and mineral jelly.

A "mineral oil" is a mixture of C15 to C40 alkanes from a non-vegetable (mineral) source. For example, a mineral oil is preferably a paraffinic oil, more preferably a naphthenic oil or even more preferably an aromatic oil. For example, a mineral oil includes nujol, light mineral oil, heavy mineral oil, paraffin oil, and liquid petrolatum. In some embodiments, light mineral oil has a density of about 0.83 to about 0.86 g/mL at 25° C. In some embodiments, heavy mineral oil has a density of about 0.875 to about 0.905 g/mL at 25° C.

A "polyglycol" is a polymer of ethylene, propylene or butylenes oxides used as a synthetic lubricant base. For example, polyglycols include polyethylene glycols (PEGs, for example with a molecular weight of about 400 to about 4000 g/mol), methoxypolyethylene glycols (MPEGs), polypropylene glycols (PPGs), polybutylene glycols (PBGs). PEGs also include for example PEG derivatives such as polyethylene glycol 40 stearate (PEG-40 stearate).

A "silicone oil" is a liquid polymerized siloxane with organic side chains. For example, a polymer that contains units of the following structural formula:

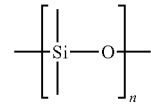

with viscosity in the range of about 5 centistokes to about 100,000 centistokes at 25° C. is also referred to as dimethicone and polydimethylsiloxane (PDMS). For example, a silicone oil includes methicone (a monomethylated linear siloxane polymer) and derivatives of linear siloxane polymers of dimethicone and methicone.

A "fluorocarbon" is a molecule consisting of carbon atoms, fluorine atoms, and at least one atom that is not fluorine such as hydrogen. In certain embodiments, a fluorocarbon is not a perfluorocarbon, i.e., a fluorocarbon having every hydrogen replaced with a fluorine atom. For example, a fluorocarbon includes 1,1,1,2-tetrafluoroethane (HFA-134a or HCFC-134a or $C_2H_2F_4$), 1-chloro-2,2,2-trifluoroethane (HFC-133a or $C_2H_2F_3Cl$), 1,1,1,3,3,3-hexafluoropropane (HFA-236fa or $C_3H_2F_6$), and 1,1,1,2,3,3,3-heptafluoropropane (HFC-227ea or $C_3HF_7$).

A "lanolin" refers to a waxy substance secreted by wool-bearing animals and encompasses lanolin derivatives. For example, lanolin includes lanolin, lanolin wax, lanolin alcohol, PEG-75 lanolin, acetylated lanolin, hydroxylated lanolin, isopropyl lanolate, and acetylated lanolin alcohol.

A "gelled mineral oil" comprises mineral oil and hydrogenated copolymer to form a gel. Example hydrogenated copolymers include hydrogenated butylene/ethylene/stryrene copolymer and hydrogenated ethylene/propylene/styrene copolymer. Example gelled mineral oils include Plastibase 50W™ and ViscUp® 160 (Lonza, Basel, Switzerland).

As used herein, the term "surfactant" refers to a surface-active agent or a substance that tends to reduce the surface tension of the liquid in which it is dissolved. Suitable surfactants include polysorbates, poloxamers, Triton, sodium dodecyl sulfate, sodium lauryl sulfate, and betaines. For example, surfactants include polyoxyethylene (20) sorbitan monolaurate (Tween® 20, e.g. from Sigma-Aldrich), polyoxyethylene (20) sorbitan monopalmitate (Tween® 40), polyoxyethylene (20) sorbitan monooleate (Tween® 80), poloxamer 188, polyoxyethylene-polyoxypropylene block copolymer (Pluronic® F-68, e.g. from Sigma-Aldrich), polyethyleneglycol 660-12-hydroxystearate (Solutol® HS 15, BASF), cocamidopropyl betaine, linoleyl betaine, myristyl betaine, cetyl betaine, polyethoxylated castor oil (Cremophor®, now Kolliphor BASF), and lecithin.

The ointments and ophthalmic formulations can be administered to the subject in conjunction with a fluorescent molecular rotor compound and an "pharmaceutically acceptable carrier" as part of a pharmaceutical composition. Pharmaceutically acceptable carriers may contain inert ingredients which do not interact with the compound. Standard pharmaceutical formulation techniques can be employed, such as those described in Remington's Pharmaceutical Sciences, Mack Publishing Company, Easton, Pa. Pharmaceutically acceptable carriers for the ophthalmic formulations include, for example, petrolatum, a mineral oil, a polyglycol, a silicone oil, a fluorocarbon, a lanolin, a gelled mineral oil, and a surfactant.

A "preservative" is a compound which can be added to the formulation to reduce bacterial activity or undesirable chemical changes in the formulations. Examples of preservatives include benzyl alcohol, ethanol, methanol, isopropanol, butyl paraben, ethyl paraben, methyl paraben, propyl paraben, cathechol, 2-chlorophenol, m-cresol, phenol, resorcinol, xylitol, 2,6-dimethylcyclohexanol, 2-methyl-2,4-pentadiol, polyvinylpyrrolidone, benzethonium chloride, merthiolate (thimersosal), benzoic acid, benzalkonium chloride, chlorobutanol, sodium benzoate, sodium propionate, and cetylpyridinium chloride.

As used herein, an "effective amount" refers to an amount of a fluorescent molecular rotor compound sufficient to diagnose or to assess risk of the target disorder. Examples of effective amounts typically range from about 0.0001 mg/kg of body weight to about 500 mg/kg of body weight. A person of ordinary skill will be able to determine an effective amount based on body weight and the nature of the fluorescent molecular rotor compound.

As used herein, the term "subject" refers to a mammal, preferably a human, but can also mean an animal in need of veterinary diagnosis or risk assessment, e.g., companion animals (e.g., dogs, cats, and the like), farm animals (e.g., cows, sheep, pigs, horses, and the like) and laboratory animals (e.g., rats, mice, guinea pigs, and the like).

It has now been discovered that an ointment comprising a fluorescent molecular rotor compound possesses advantageous properties (e.g., uniformity of particle content) when it is manufactured by methods described and claimed herein, wherein these properties render the ointment particularly suitable for administration to ocular tissue, preferably for administration to the lens. For example, ointments of the present invention can be manufactured by a method comprising:

(a) combining a fluorescent molecular rotor compound with mineral oil as a levigating agent, thereby obtaining a first mixture;
(b) subjecting the first mixture to ball milling agitation with a grinding media, thereby obtaining a second mixture; and
(c) combining the second mixture with a hydrophobic vehicle, thereby obtaining an ointment.

In some embodiments, the process includes a second mixture comprising particles of the fluorescent molecular rotor compound, the particles having a size distribution characterized by a d(0.9) to a d(0.99) of less than 10 microns. For example, the particles can have a size distribution characterized by a d(0.95) particle size from about 1 to about 25 microns. Example embodiments have a size distribution characterized by a d(0.95) particle size from about 5 to about 20 microns. For example, the particles can have a size distribution characterized by a d(0.95) particle size of less than about 10 microns.

In one embodiment, the median particle size diameter is less than 10 μm, preferably less than 9 μm, more preferably less than 8 μm, even more preferably less than 7 μm and most preferably less than 6 μm. Preferably, the median particle diameter in the range from 2 to 10 μm, more preferably in the range from 3 to 8 μm and even more preferably from 4 to 7 μm. Most preferably, the median particle diameter is between 4 and 6 μm.

Particle size of the fluorescent molecular rotor compound can be determined by laser light diffraction, transmission electron microscopy, scanning electron microscopy, light microscopy, X-ray diffractometry and light scattering methods or Coulter counter analysis (see, for example, "Characterization of Bulk Solids" D. McGlinchey, Ed., Blackwell Publishing, 2005). For example, the particle size of a fluorescent molecular rotor compound can be determined using a laser light diffraction analyzer for particle size analysis manufactured by Malvern instruments, model Mastersizer 2000 with wet sampling system manufactured by Malvern, model number Hydro 2000S. The d(0.95) for all samples can be calculated using the software provided by Malvern instruments for the model Mastersizer 2000.

For example, the grinding media can comprise beads with an average size or diameter of 0.03, 0.05, 0.1, 0.2, 0.3, 0.4, 0.5, 0.65, 0.8, 1, 1.25, 1.5, 1.75, 2, 2.3, 2.7, 3, 5, 10, 15, 20, and 25 mm. In some embodiments, the process includes grinding media for ball milling agitation comprises particles with an average size of at least 3 mm.

In some embodiments, the grinding media is a ceramic selected from the group consisting of magnesia stabilized zirconia, zirconium silicate, zirconia stabilized alumina, alumina-zirconia composite, burundum, and yttrium stabilized zirconia. Preferably, the grinding media comprises magnesia stabilized zirconia, more preferably zirconium silicate, even more preferably zirconia stabilized alumina, even more preferably alumina-zirconia composite and most preferably burundum. In some embodiments the grinding media is yttrium stabilized zirconia such as YTZ® grinding media (Tosoh Corp., Tokyo, Japan).

In some embodiments, the process includes a ratio of the grinding media volume to the weight of mineral oil and fluorescent molecular rotor compound ranging from about 0.05 to about 0.7. For example, 7 mL of YTZ® grinding media can be mixed with about 10 g of mineral oil and about 0.5 g of fluorescent molecular rotor compound for a ratio of about 0.67. In some embodiments the ratio of grinding media volume to mineral oil and fluorescent molecular rotor compound is about 0.26.

In one embodiment, the hydrophobic vehicle is selected from one or more of a petrolatum, a mineral oil, a polyglycol, a silicone oil, a fluorocarbon, a lanolin, a gelled mineral oil, and a surfactant. In some embodiments, the hydrophobic vehicle is selected from one or more of a petrolatum and a mineral oil. For example, the hydrophobic vehicle can be a combination of heavy mineral oil and white petroleum. Table 1 below outlines example vehicle formulations that can be used in the ointments of the invention. Column 1 denotes a formulation name while columns 2 and 3 outline the amount of components (mg) to be used in every gram of the formulation. For example, the 80/20 vehicle comprises 80% white petroleum (800 mg of white petroleum per 1 g of ointment) and 20% heavy mineral oil (200 mg of white petroleum per 1 g of ointment). In some embodiments, the ophthalmic ointment comprises Compound 11 at 0.5% (w/w or 5 mg of Compound 11 per g of ointment), 20% heavy mineral oil (199 mg of white petroleum per 1 g of ointment), and 80% white petroleum (796 mg of white petroleum per 1 g of ointment).

TABLE 1

Example ointment preparations of the invention.

| Formulation | Component | Component Conc. (mg/g) |
|---|---|---|
| 80/20 Vehicle | Heavy mineral oil, USP | 200 |
| | White Petroleum, USP | 800 |
| 75/25 Vehicle | Heavy mineral oil, USP | 250 |
| | White Petroleum, USP | 750 |
| 70/30 Vehicle | Heavy mineral oil, USP | 300 |
| | White Petroleum, USP | 700 |
| 80/20 Ointment with 0.5% (w/w) Compound 11 | Compound 11 | 5 |
| | Heavy mineral oil, USP | 199 |
| | White Petroleum, USP | 796 |

In some embodiments, the ointment can be filled into bottles with a controlled dropper tip, bottles with a natural stream tip, 1 mL syringes, and tubes as containers to dispense the ointment.

The ointment or ophthalmic formulation can be sterilized by methods known in the art before administration to subjects. For example, the ointment can be sterilized by electron beam irradiation. In some embodiments, the electron beam exposure can be in the range of 14 kGy to 21 kGy. In preferred embodiments, the components of the ointment are sterilized before manufacture and preparation of the ointment by heat or electron beam irradiation. The process for preparing an ointment can also include sterilization by irradiating the fluorescent molecular rotor compound and the mineral oil before forming the first mixture to undergo ball milling agitation. In some embodiments, the first mixture can also be sterilized by electron beam irradiation after combining the fluorescent molecular rotor compound and the mineral oil but before ball milling agitation. The percent area of the fluorescent molecular rotor compound in the irradiated samples can be compared to a non-irradiated sample as determined by the concentration analysis described in Example 3. Changes in the relative area of the related substance peak compared to the area of the fluorescent molecular rotor compound before and after irradiation can be compared to evaluate degradation of the fluorescent molecular rotor compound due to formulation and ointment irradiation.

For example, processes to prepare ointments of the invention include an ointment that can be used for diagnostic purposes to detect and diagnose neurodegenerative diseases. The processes of the invention can be used to prepare an ointment that can be used for diagnostic purposes by contacting an ocular tissue of a subject, e.g., a human subject, with the fluorescent molecular rotor compound which binds to an amyloid protein or pre-amyloid protein aggregate. The fluorescent molecular rotor compound preferentially binds to amyloid proteins compared to other β-pleated sheet containing proteins. Neurodegenerative diseases such as amyloidogenic disorders have recently been linked to the presence or increase in the amount of aggregate in the supranuclear region and/or cortical lens region of the eye. In a preferred embodiment of the invention, the ointment is used in diagnosis or for aiding in a diagnostic method. Such a method may involve determining the amount of amyloid aggregate in the supranuclear region and/or cortical lens region of the eye. Preferably, the ointment, for example, is used in diagnosis of amyloidogenic disorders such as Alzheimer's Disease (AD), Familial AD, Sporadic AD, Creutzfeld-Jakob disease, variant Creutzfeld-Jakob disease, spongiform encephalopathies, Prion diseases (including scrapie, bovine spongiform encephalopathy, and other veterinary prionopathies), Parkinson's disease, Huntington's disease (and trinucleotide repeat diseases), amyotrophic lateral sclerosis, Down's Syndrome (Trisomy 21), Pick's Disease (Frontotemporal Dementia), Lewy Body Disease, neurodegeneration with brain iron accumulation (Hallervorden-Spatz Disease), synucleinopathies (including Parkinson's disease, multiple system atrophy, dementia with Lewy Bodies, and others), neuronal intranuclear inclusion disease, tauopathies (including progressive supranuclear palsy, corticobasal degeneration, hereditary frontotemporal dementia (with or without Parkinsonism), and Guam amyotrophic lateral sclerosis/parkinsonism dementia complex. These disorders may occur alone or in various combinations. Aggregate analysis is also useful to detect Transmissible Spongiform Encephalopathies (TSEs), which are prion-mediated diseases characterized by fatal spongiform neurodegeneration of the brain and are associated with severe and fatal neurological signs and symptoms. TSE prionopathies include Creutzfeld-Jacob Disease (CJD); new variant, Creutzfeld-Jacob Disease (nv-CJD); Gertsmann-Straussler-Scheinker syndrome; fatal familial insomnia; Kuru; Alpers Syndrome; Bovine Spongiform Encephalopathy (BSE); scrapie; and chronic wasting disease (CWD).

For example, the ointments and ophthalmic formulations can utilize amyloid-binding bioavailable lipophilic fluorescent molecular rotor compounds to detect amyloid peptides in the eye. Examples of fluorescent molecular rotor compounds that have been used to analyze brain tissue (but not eye tissue) include X-34 and {(trans, trans)-1-bromo-2,5-bis-(3-hydroxycarbonyl-4-hydroxy)styrylbenzene (BSB)} (Styren et al., 2000, *J. Histochem.*, 48:1223-1232; Link et al., 2001, *Neurobiol. Aging*, 22:217-226; and Skovronsky et al., 2000, *Proc. Natl., Acad. Sci. U.S.A.*, 97(13):7609-7614). These fluorescent molecular rotor compounds emit light in the blue-green range, thus the level of fluorescence, which is diagnostically relevant, exceeds the amount of human lens autofluorescence in the blue-green range. For example, other useful fluorescent molecular rotor compounds include Me-X04 (1,4-bis(4'-hydroxystyryl)-2-methoxybenzene), Chrysamine or Chrysamine derivative compounds such as {(trans, trans)-1-bromo-2,5-bis-(3-hydroxycarbonyl-4-hydroxy)styrylbenzene (BSB)}. Such compounds are described in Mathis et al., *Curr. Pharm. Des.*, 10(13):1469-93 (2004); U.S. Pat. Nos. 6,417,178; 6,168,776; 6,133,259; and 6,114,175, each of which is hereby incorporated by reference in its entirety. Nonspecific amyloidphilic fluorescent molecular rotor compounds such as thioflavin T, thioflavin S or Congo red dye may also be used. For example, the following structural formulas may be fluorescent molecular rotor compounds:

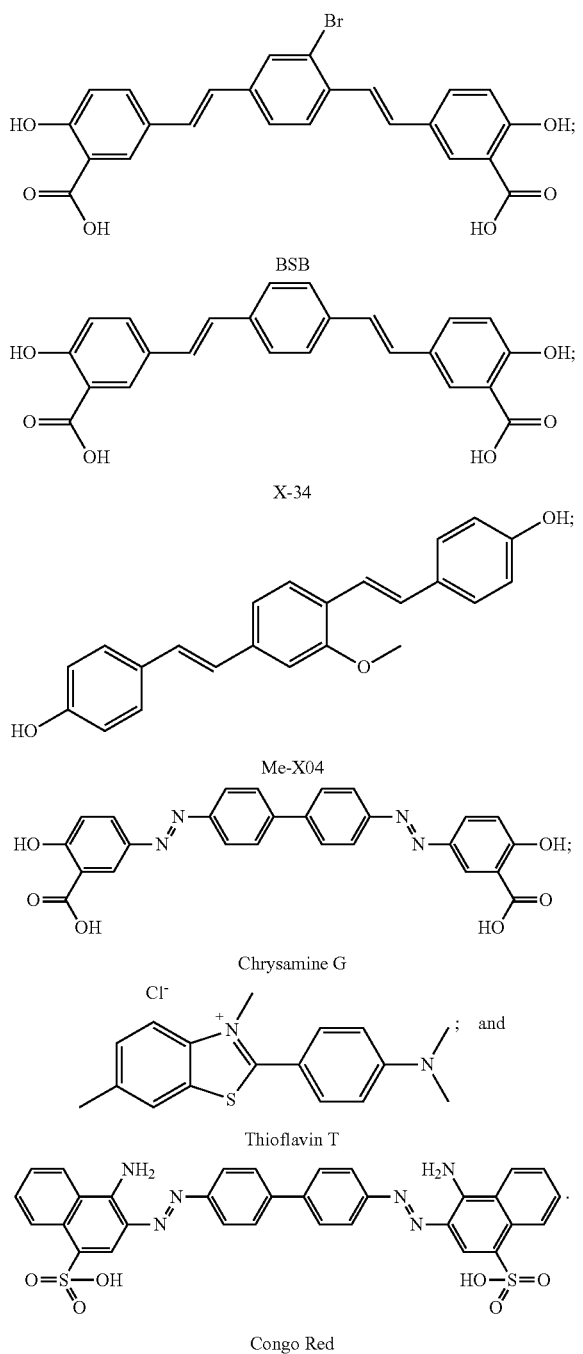

BSB

X-34

Me-X04

Chrysamine G

Thioflavin T

Congo Red

In one embodiment, the fluorescent molecular rotor compound is represented by structural Formula (I), or a pharmaceutically acceptable salt thereof:

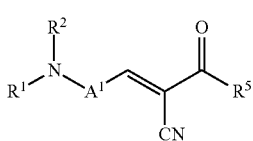
(I)

wherein:

$A^1$ is an optionally substituted C6-C18 arylene, an optionally substituted C5-C18 heteroarylene, or is represented by the following structural formula:

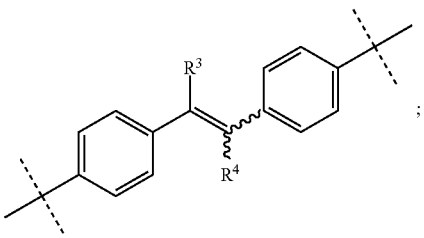

$R^1$ and $R^2$ are each independently hydrogen, optionally substituted C1-C12 alkyl, an optionally substituted C1-C12 heteroalkyl, optionally substituted C3-C12 cycloalkyl, or $R^1$ and $R^2$ taken together with the nitrogen atom to which they are attached form an optionally substituted 3 to 12 membered heterocycloalkyl;

$R^3$ and $R^4$ are each independently hydrogen, methyl, or ethyl;

$R^5$ is —OH, optionally substituted —O(C1-C6 alkyl), —NR$^6$R$^7$, or is represented by the following structural formula:

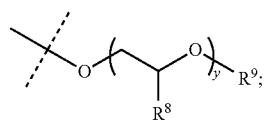

$R^6$ and $R^7$ are each independently, hydrogen, methyl, ethyl, or $R^6$ and $R^7$ taken together with the nitrogen atom to which they are attached form a 5 to 7 membered heterocycloalkyl containing one to three ring heteroatoms independently selected from N, O, and S;

wherein:

y is an integer from 1 to 10;

$R^8$, for each occurrence independently, is hydrogen, —OH, or —CH$_2$OH;

$R^9$ is hydrogen, —NR$^{10}$R$^{11}$, —C(O)R$^{12}$, optionally substituted C1-C6 alkyl, or optionally substituted C1-C6 heteroalkyl;

$R^{10}$, $R^{11}$ and $R^{12}$ are each independently hydrogen or C1-C6 alkyl.

In some embodiments, $A^1$ is selected from the group consisting of an optionally substituted phenyl, an optionally substituted naphthyl, an optionally substituted (E)-stilbene, or an optionally substituted (Z)-stilbene. In another embodiment, $A^1$ is an optionally substituted naphthyl. Values and preferred values of the remainder of the variables are as defined above and below with respect to Formula (I).

In a preferred embodiment, the fluorescent molecular rotor compound, which is used in a process for preparing an ophthalmic ointment is a compound according to structural Formula (II). The compound of Formula (II) is a compound of Formula (I), wherein $A^1$ is represented by the following structural formula:

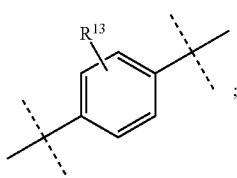

and is represented by the following structural Formula (II), or a pharmaceutically acceptable salt thereof:

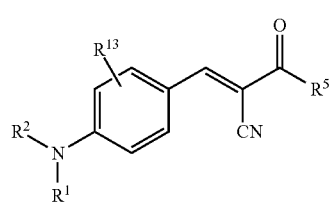

(II)

wherein:
$R^{13}$ is hydrogen, —OH, or optionally substituted —O(C1-C6 alkyl). Values and preferred values of the remainder of the variables are as defined above and below with respect to Formula (I).

In a preferred embodiment, the fluorescent molecular rotor compound, which is used in a process for preparing an ophthalmic ointment is a compound according to structural Formula (III). The compound of Formula (III) is a compound of Formula (I), wherein $A^1$ is represented by the following structural formula:

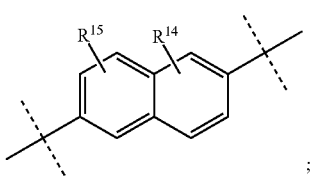

and is represented by the following structural Formula (III), or a pharmaceutically acceptable salt thereof:

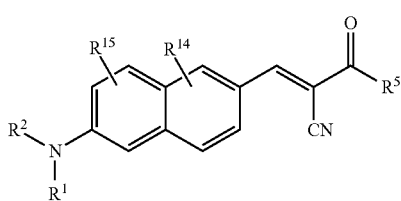

(III)

wherein:
$R^{14}$ and $R^{15}$ are each independently hydrogen, —OH, or optionally substituted —O(C1-C6 alkyl).

Values and preferred values of the remainder of the variables are as defined above and below with respect to Formula (I).

In some embodiments, $R^1$ and $R^2$ are both optionally substituted C1-C12 alkyl. In other embodiments, $R^1$ and $R^2$ are both selected from the group consisting of methyl, ethyl, propyl, and butyl. Values and preferred values of the remainder of the variables are as defined above and below with respect to Formula (I).

In some embodiments, $R^1$ and $R^2$ taken together with the nitrogen atom to which they are attached form an optionally substituted 3 to 12 membered heterocycloalkyl. In another embodiment, $R^1$ and $R^2$ taken together with the nitrogen atom to which they are attached form heterocycloalkyl selected from the group consisting of piperidine, morpholine, piperazine, and 1-methylpiperazine. Values and preferred values of the remainder of the variables are as defined above and below with respect to Formula (I), Formula (II), or Formula (III).

In some embodiments, $R^5$ is

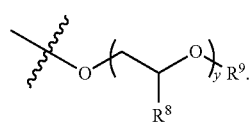

Values and preferred values of the remainder of the variables are as defined above and below with respect to Formula (I), Formula (II), or Formula (III).

In some embodiments, $R^5$ is

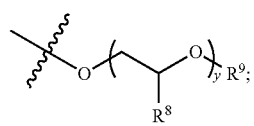

y is 1;
$R^8$ is —CH$_2$OH; and
$R^9$ is —OH.

Values and preferred values of the remainder of the variables are as defined above and below with respect to Formula (I), Formula (II), or Formula (III).

In some embodiments, $R^5$ is

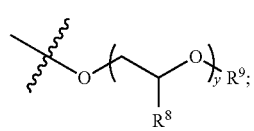

y is 3; and
$R^9$ is methyl.

Values and preferred values of the remainder of the variables are as defined above and below with respect to Formula (I), Formula (II), or Formula (III).

In some embodiments, $R^5$ is

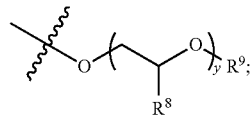

y is 4; and
$R^9$ is methyl.

Values and preferred values of the remainder of the variables are as defined above and below with respect to Formula (I), Formula (II), or Formula (III).

In some embodiments, $A^1$ is selected from the group consisting of an optionally substituted phenyl, an optionally substituted naphthyl, an optionally substituted (E)-stilbene, or an optionally substituted (Z)-stilbene; $R^1$ and $R^2$ are both optionally substituted C1-C12 alkyl; and $R^5$ is

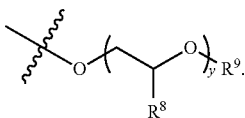

Values and preferred values of the remainder of the variables are as defined above and below with respect to Formula (I).

In some embodiments, $A^1$ is selected from the group consisting of an optionally substituted phenyl, an optionally substituted naphthyl, an optionally substituted (E)-stilbene, or an optionally substituted (Z)-stilbene; $R^1$ and $R^2$ taken together with the nitrogen atom to which they are attached form an optionally substituted 3 to 12 membered heterocycloalkyl; and $R^5$ is

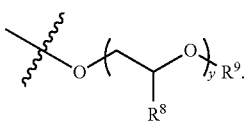

Values and preferred values of the remainder of the variables are as defined above and below with respect to Formula (I).

In some embodiments, $A^1$ is an optionally substituted phenyl; $R^1$ and $R^2$ are both optionally substituted C1-C12 alkyl; and $R^5$ is

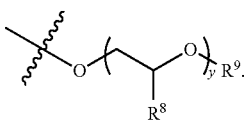

Values and preferred values of the remainder of the variables are as defined above and below with respect to Formula (I).

In some embodiments, $A^1$ is an optionally substituted phenyl; $R^1$ and $R^2$ taken together with the nitrogen atom to which they are attached form an optionally substituted 3 to 12 membered heterocycloalkyl; and $R^5$ is

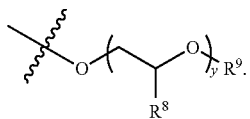

Values and preferred values of the remainder of the variables are as defined above and below with respect to Formula (I).

In some embodiments, $A^1$ is an optionally substituted naphthyl; $R^1$ and $R^2$ are both optionally substituted C1-C12 alkyl; and $R^5$ is

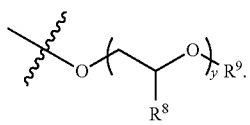

Values and preferred values of the remainder of the variables are as defined above and below with respect to Formula (I).

In some embodiments, $A^1$ is an optionally substituted naphthyl; $R^1$ and $R^2$ taken together with the nitrogen atom to which they are attached form an optionally substituted 3 to 12 membered heterocycloalkyl; and $R^5$ is

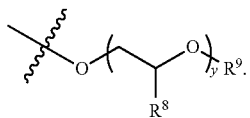

Values and preferred values of the remainder of the variables are as defined above and below with respect to Formula (I).

In some embodiments, the fluorescent molecular rotor compound is selected from the group consisting of:

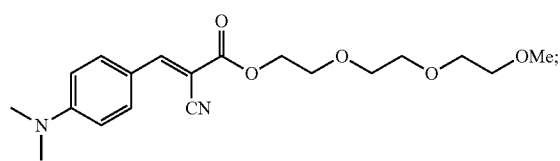

8a

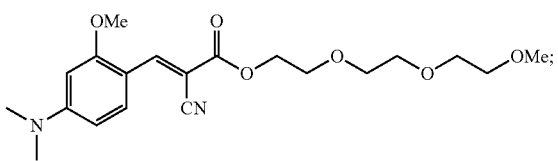

8b

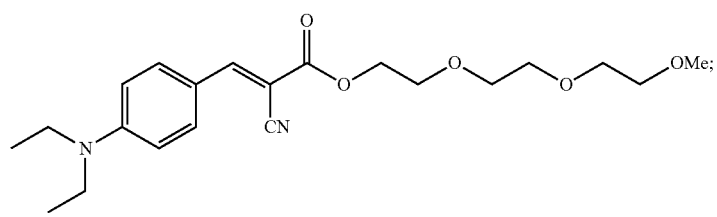

8c

-continued
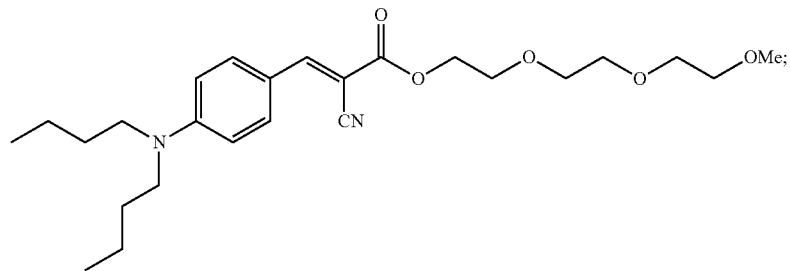
8d
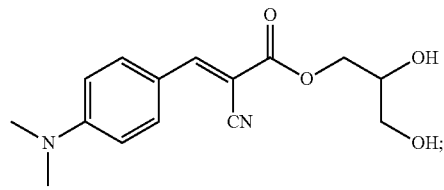
14
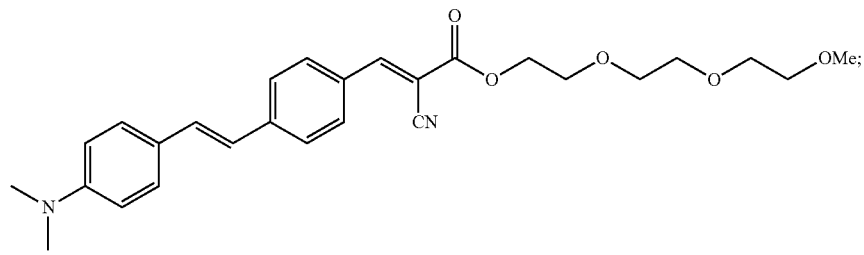
19
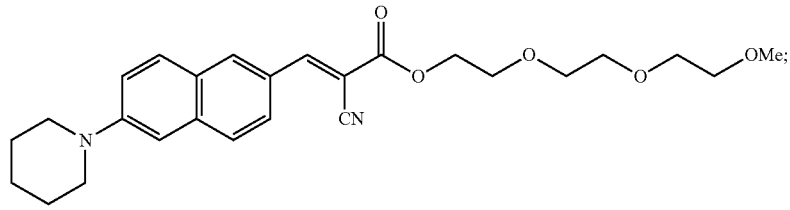
11
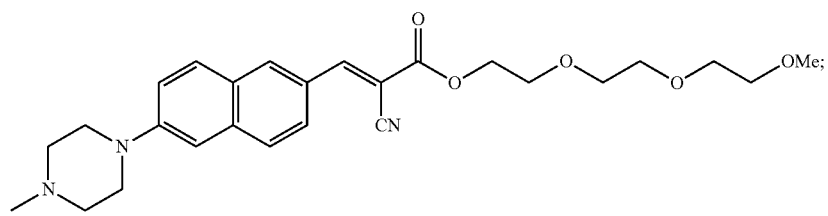
28
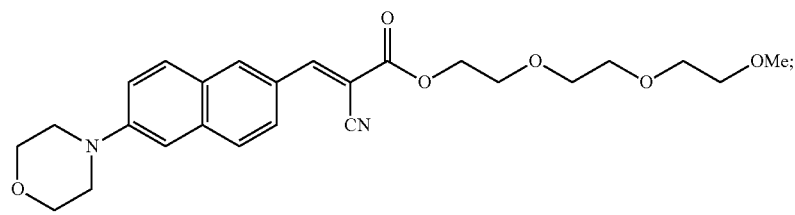
29
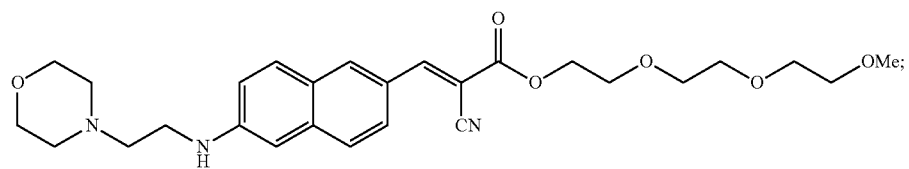
30

-continued

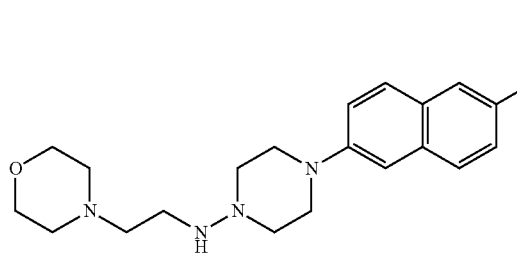

31

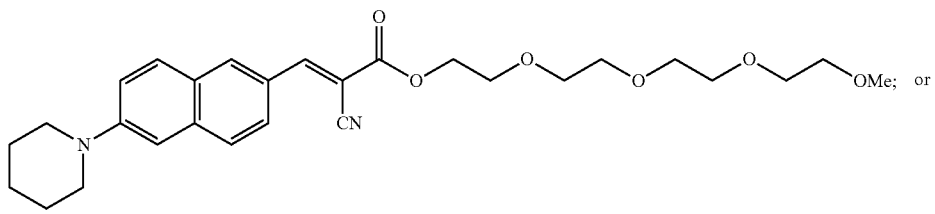

33

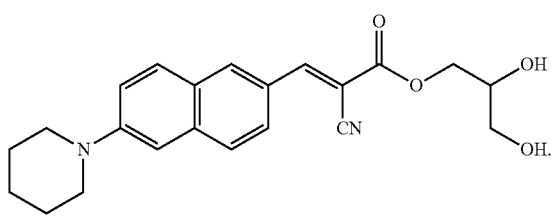

In some embodiments, the present invention relates to an ophthalmic formulation comprising an effective amount of a compound of the following structural Formula (I), structural Formula (II), or structural Formula (III), or a pharmaceutically acceptable salt thereof:

(I)

$$\underset{R^1}{\overset{R^2}{N}}-A^1\underset{CN}{\overset{}{=}}\overset{O}{\underset{}{\parallel}}R^5;$$

(II)

$$R^{13}\text{—}\text{Ar}\text{—}\overset{}{=}\underset{CN}{\overset{O}{\parallel}}R^5; \text{ or}$$
with $R^2$, $R^1$—N substituent (III)

$$R^{15}, R^{14}\text{—naphthyl—}\overset{}{=}\underset{CN}{\overset{O}{\parallel}}R^5;$$
with $R^2$, $R^1$—N substituent and a pharmaceutically acceptable carrier.

The fluorescent molecular rotor compounds of structural Formula (I) can be synthesized by any methods known to those of skill in the art. For example, suitable fluorescent molecular rotor compounds can be synthesized by the methods described in PCT Publication WO 2011/072257, which is hereby incorporated by reference in its entirety.

EXEMPLIFICATION

Example 1

Optimization of Ball Milling Agitation Conditions for Mixtures of Fluorescent Molecular Rotor Compounds in Mineral Oil Experiments were conducted to test whether the particle size of the grinding media used for ball milling agitation affected the fluorescent molecular rotor compound particle size. Mixtures of Compound 11 HCl salt in heavy mineral oil were subjected to ball milling agitation with grinding media YTZ® beads with an average diameter of 0.5 mm, 2 mm, and 5 mm.

Grinding media consisting of 5.0703 g of YTZ® beads with an average diameter of 0.5 mm (a yttrium stabilized zirconia ceramic grinding media, Tosoh Corp., Tokyo, Japan), 0.5043 g of Compound 11 HCl salt, and 9.9775 g of heavy mineral oil (Spectrum Chemicals) were added to a 20 mL amber glass bottle. The bottle containing the mixture was placed on a US Stoneware Ball Mill (SN CZ-92040) at a speed setting of 25, which corresponds to about 50 rpm, for ball milling agitation for one day. Visual inspection showed large chunks of Compound 11 salt remaining after 1 day. The appearance did not change significantly upon continued ball milling agitation for an additional 3 days (4 days total). Since increasing the amount of time of ball milling agitation did not affect Compound 11 particle size, an additional 20.73 g of YTZ® grinding media was added to the mixture. The mixture was then allowed to undergo ball milling agitation for one more day. Afterwards, most of the large chunks of Compound 11 salt were gone.

Further experiments were performed using larger size YTZ® grinding media with average diameters of 5 mm and 2 mm (yttrium stabilized zirconia ceramic grinding media, Tosoh Corp., Tokyo, Japan) to evaluate whether increasing the particle size of the grinding media could decrease the time of ball milling agitation. A mixture of 10.22 g of YTZ® beads with an average diameter of 5 mm (Tosoh Corp., Tokyo, Japan), 0.5048 g of Compound 11 HCl salt and 10.02 g of heavy mineral oil (Spectrum Chemicals) were added to a 20 mL amber glass bottle before ball milling agitation using a US Stoneware Ball Mill for three days. A mixture of 5.09 g of YTZ® beads with an average diameter of 2 mm (Tosoh Corp., Tokyo, Japan), 0.5013 g of Compound 11 HCl salt and 9.94 g of heavy mineral oil (Spectrum Chemicals) were added to a 20 mL amber glass bottle before ball milling agitation using a US Stoneware Ball Mill for three days. Visual inspection showed that the process using 5 mm compared to 2 mm YTZ® beads as grinding media produced a more homogeneous mixture after 3 days of ball milling agitation. Processes using grinding media with larger average bead diameter (5 mm compared to 2 mm and 0.5 mm) increased the uniformity of the mixture of heavy mineral oil and Compound 11 particles, which was desirable for first mixtures used to prepare final ointments of the invention. Also, grinding media with smaller average bead diameter can create practical problems for handling such as recovering material from the surface of the beads.

Example 2

Microscopic Examination of Mixture after Ball Milling Agitation to Evaluate Uniformity Microscopic examination of mixtures after ball milling can be used to assess uniformity and to estimate the particle size of the fluorescent molecular rotor compounds. Microscopic examination of the mixtures containing Compound 11 were performed using a compound optical microscope with a calibrated eyepiece micrometer, or reticle. For example, the eyepiece micrometer, reticle, can be aligned and calibrated with the stage micrometer by aligning the zero line of the reticle with the zero line of the stage micrometer, and the ratios between the micrometers or scales can be used to determine sizes and distances. The microscopic analysis showed predominately fine particles using the 0.5 mm grinding media beads for the ball milling process after ball milling agitation for 4 days, but the measured concentration for this mixture was inconsistent with the expected concentration. Microscopic examination of the mixture of Compound 11 HCl salt in heavy mineral oil subjected to ball milling agitation with YTZ® beads with an average diameter of 5 mm was more homogenous than the process using YTZ® beads with an average diameter of 2 mm (Tosoh Corp., Tokyo, Japan), which showed a range of sizes of Compound 11 particles. Microscopic examination showed a uniform mixture of particles approximately 5 microns in diameter, which was within the target range for fluorescent molecular rotor compound particle size, with the process using the 5 mm grinding media beads.

Example 3

HPLC Analysis of Concentration of Fluorescent Molecular Rotor Compounds in Mixtures The following HPLC method was used to analyze whether the concentration of fluorescent molecular rotor compounds in mixtures of mineral oil and Compound 11 was consistent with the expected concentration of the mixture. The HPLC analysis was also used to evaluate degradation of Compound 11 in the mixture. The HPLC instrument used was a Waters 2695 Separation Module, or equivalent containing a pump capable of delivering a gradient flow rate of 1.0 mL/min or equivalent and a Waters 2487 Multiwavelength Detector, or dual wavelength detector capable of detection at 215 nm and 320 nm, or equivalent. The column used was a Waters Deltapak C18 column, 5 μm, 3.9×150 mm, (Waters Corp., Milford, Mass., Catalog No.: WAT011793). The flow rate was 1.0 mL/min with detection at a wavelength of 215 nm and a column temperature of 25° C. The injection volume used for the concentration sample evaluation was 20 μL and for the related substances sample evaluation was 50 μL. The mobile phases were A: 0.1% trifluoroacetic acid in water, C: methanol, and D: ethanol, and the gradient program shown in Table 2 was used for the HPLC method.

TABLE 2

Example mobile phase gradient program.

| Time (min) | % A | % C | % D |
|---|---|---|---|
| 0 | 50 | 50 | 0 |
| 10 | 50 | 50 | 0 |
| 12 | 0 | 100 | 0 |
| 14 | 0 | 0 | 100 |
| 18 | 0 | 0 | 100 |
| 20 | 0 | 100 | 0 |
| 22 | 50 | 50 | 0 |
| 32 | 50 | 50 | 0 |

Table 3 shows the sample components found by HPLC analysis with the approximate retention time (RT) and relative retention time (RRT), which is calculated as a ratio relative to the retention time of Compound 11 (8.5 min). In a mixture sample compared to a standard sample, increased relative peak area of the related substance peak (RT of 3.8 min, Table 3) compared to the peak area of Compound 11 (RT of 8.5 min, Table 3) would indicate degradation of Compound 11. The concentration in the mixture sample of Compound 11 was determined by analyzing the HPLC peak with a retention time of 8.5 min (Table 3) compared to a standard sample of Compound 11.

TABLE 3

Example retention times (RT) and percentages of components detected.

| Component | Approximate RT | % Detected |
|---|---|---|
| Related Substance | 3.8 min | 0.23% |
| Compound 11 | 8.5 min | 99.77% |
| Unknown | 9.2 min | N/A |

The HPLC analysis showed no significant degradation of Compound 11 based on changes in the related substance peak (RT of 3.8 min, Table 3), which corresponds to a peak that appears after forced degradation, after ball milling agitation. However, the concentration of the mixture of Compound 11 and heavy mineral oil after ball milling agitation with YTZ® grinding media beads of an average diameter of 0.5 mm was determined by HPLC (RT of 8.5 min, Table 3) to be 4.75 mg/g as compared to an expected concentration of 48.12 mg/g (504.3 mg/10.48 g, mineral oil and Compound 11). The concentration discrepancy indicated that Compound 11 was not uniformly dispersed in the mixture and that ball milling agitation with 0.5 mm beads provided unacceptable mixtures. The concentration as measured by HPLC of the mixture of Compound 11 and heavy mineral oil after ball milling agitation with beads of an average diameter of 5 mm was 44.9 mg/g as compared to an expected concentration of 47.98 mg/g (504.8 mg/10.52 g, mineral oil and Compound 11), which was within the acceptable range. The process of the invention using ball milling agitation with YTZ® 5 mm beads provided a mixture with an acceptable concentration of Compound 11 without degradation of Compound 11 as analyzed by HPLC.

Example 4

Preparation of Ointment Formulations with Fluorescent Molecular Rotor Compounds

Based on optimized ratios of vehicle components for ointment consistency, ointments can be prepared using the claimed process. A mixture of 10.22 g of YTZ® beads with an average diameter of 5 mm (Tosoh Corp., Tokyo, Japan), 0.5048 g of Compound 11 HCl salt and 10.02 g of heavy mineral oil (Spectrum Chemicals) is added to a 20 mL amber glass bottle. The mixture is subjected to ball milling agitation using a US Stoneware Ball Mill for three days. After removing the grinding media beads, the mixture is added to a mixture containing about 10 g of heavy mineral oil and about 79.5 g of white petroleum. The ointment has a calculated concentration of:

504.8 mg/(10.02 g+0.5048 g+10 g+80 g)=504.8 mg/100.5248 g or 5.02 mg/g of Compound 11 in the final ointment or 0.5% (w/w) Compound 11.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A process for preparing an ophthalmic ointment, comprising:

(a) combining a fluorescent molecular rotor compound of the following structural formula:

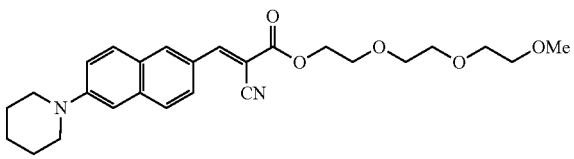 [SMILES: COCCOCCOCCOC(=O)/C(C#N)=C/c1ccc2cc(N3CCCCC3)ccc2c1]

with mineral oil as a levigating agent, thereby obtaining a first mixture;

(b) subjecting the first mixture to ball milling agitation with a grinding media that includes beads with an average particle size of from 3mm to 8 mm, thereby obtaining a second mixture; wherein the ball milling agitation is conducted in a container having a ball milling container volume, the grinding media has a grinding media volume, and a ratio of the grinding media volume to the ball milling container volume ranges from about 0.05 to about 0.35; and (c) combining the second mixture with a hydrophobic vehicle, thereby obtaining an ointment wherein the fluorescent molecular rotor compound is in the form of particles having a d(0.95) particle size of less than about 10 microns.

2. The process of claim 1, wherein the grinding media for ball milling agitation comprises beads with an average size from 4mm to 6mm.

3. The process of claim 2, wherein the grinding media for ball milling agitation comprises beads with an average size of 5 mm.

4. The process of claim 3, wherein the second mixture comprises particles of the fluorescent molecular rotor compound, the particles having a size distribution characterized by a d(0.95) particle size of 5 microns in diameter.

5. The process of claim 1, wherein the grinding media is a ceramic selected from the group consisting of magnesia stabilized zirconia, zirconium silicate, zirconia stabilized alumina, alumina-zirconia composite, burundum, and yttrium stabilized zirconia.

6. The process of claim 5, wherein the grinding media is yttrium stabilized zirconia.

7. The process of claim 1, wherein the hydrophobic vehicle is selected from one of more of: a petrolatum, a mineral oil, a polyglycol, a silicone oil, a fluorocarbon, a lanolin, a gelled mineral oil, and a surfactant.

8. The process of claim 7, wherein the hydrophobic vehicle is selected from one or more of a petrolatum and a mineral oil.

9. The process of claim 1, further comprising irradiating the fluorescent molecular rotor compound and the mineral oil before forming the first mixture.

10. The process of claim 1, further comprising irradiating the first mixture.

* * * * *